United States Patent
Bertassi et al.

(10) Patent No.: US 8,062,598 B2
(45) Date of Patent: Nov. 22, 2011

(54) VOLATILE SUBSTANCES DIFFUSER

(75) Inventors: Edoardo Bertassi, Trento (IT); David Moreno, Cerdanyola del Valles (ES); José Antonio Muñoz, Cerdanyola del Valles (ES); Cedric Morhain, Cerdanyola del Valles (ES)

(73) Assignee: Zobele Holding Spa, Trento (IT)

( * ) Notice: Subject to any disclaimer, the term of this patent is extended or adjusted under 35 U.S.C. 154(b) by 473 days.

(21) Appl. No.: 12/135,589

(22) Filed: Jun. 9, 2008

(65) Prior Publication Data
US 2008/0305002 A1 Dec. 11, 2008

Related U.S. Application Data

(60) Provisional application No. 60/942,586, filed on Jun. 7, 2007.

(51) Int. Cl.
*A61L 9/00* (2006.01)
(52) U.S. Cl. ............. 422/123; 422/124; 239/58; 239/59
(58) Field of Classification Search .................... 239/58, 239/59
See application file for complete search history.

(56) References Cited

U.S. PATENT DOCUMENTS

| 4,268,285 | A | | 5/1981 | Mason |
| 4,361,279 | A | * | 11/1982 | Beacham ..................... 239/56 |
| 5,575,992 | A | | 11/1996 | Kunze |
| 2006/0032937 | A1 | | 2/2006 | Caserta et al. |

FOREIGN PATENT DOCUMENTS

| EP | 1082970 A1 | 3/2001 |
| EP | 0923386 B1 | 8/2001 |
| EP | 1698355 A1 | 9/2006 |
| JP | 02252462 | 10/1990 |
| WO | WO97/42982 | 11/1997 |
| WO | WO2005/014061 | 2/2005 |
| WO | WO2006/084921 | 8/2006 |
| WO | WO 2007/048178 | 5/2007 |

OTHER PUBLICATIONS

International Search Report and Written Opinion, dated Oct. 1, 2008, issued in International Application No. PCT/EP2008/057069.

* cited by examiner

*Primary Examiner* — Sean E Conley
(74) *Attorney, Agent, or Firm* — Knobbe Martens Olson & Bear, LLP

(57) ABSTRACT

The present invention refers to a volatile substance diffuser based on permeable membrane with a closure where a solid wall is applied to or separated from the membrane to stop or allow evaporation, respectively. The shape of the membrane is adapted to compensate possible vacuum inside the container.

26 Claims, 18 Drawing Sheets

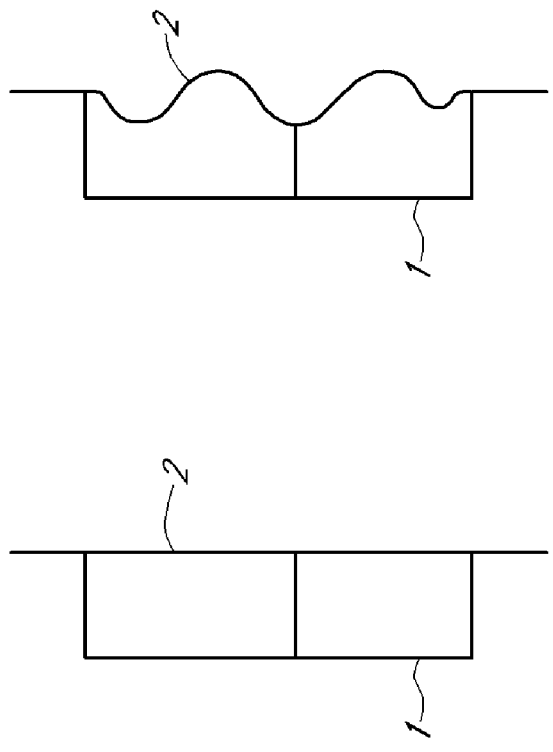
FIG. 2D
FIG. 2C
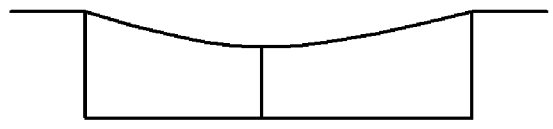
FIG. 2B
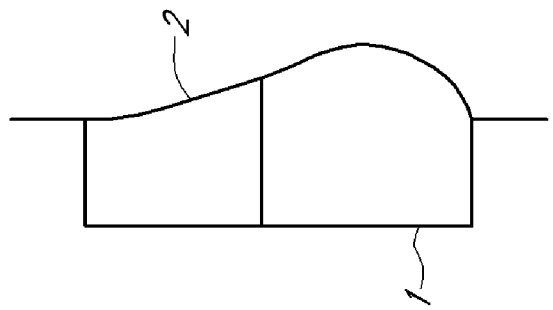
FIG. 2A

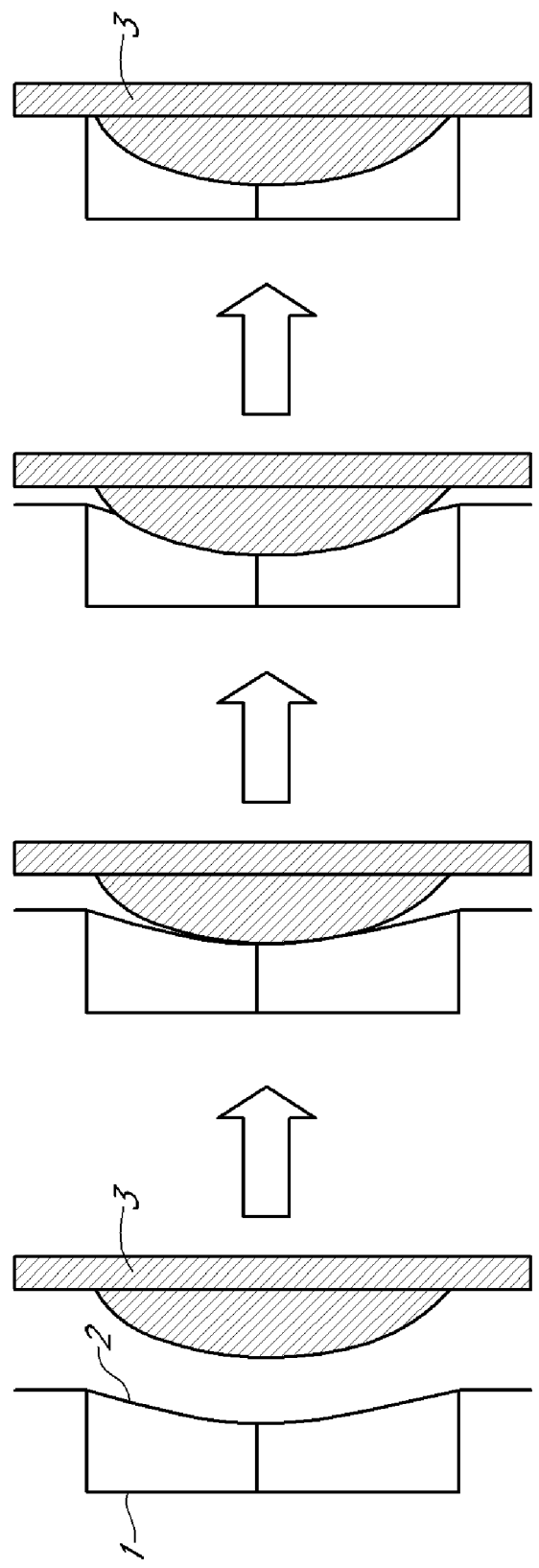

VOLATILE SUBSTANCES DIFFUSER

RELATED APPLICATIONS

This application claims the benefit under 35 U.S.C. §119 (e) of U.S. Provisional Application No. 60/942,586, filed Jun. 7, 2007 which is incorporated herein by reference in its entirety.

BACKGROUND OF THE INVENTION

Some of the existing solutions of the prior art are described in the following patents: EP-0.923.386 B1 (FIG. 1a), EP-1.082.970A1 (FIG. 1b), EP-1.698.355A1 (FIG. 1c).

Containers with membrane having two or more compartments for containing volatile substances of different nature are known in the state of the art. This is the case of the patents EP-1.082.970, WO-06084921 and EP-1.698.355.

Evaporation of two different volatile substances thorough membranes of different containers is also disclosed in the Japanese patent JP-02252462, although for a different purpose of the device object of the present invention.

Other documents generally related to the use of evaporation of volatile substances thorough semi-permeable membranes are: EP-0.923.386, U.S. Pat. No. 5,575,992, WO-05014061 and WO-97/42982.

All above inventions do not provide any means to release a fragrance A and, at the same time, appreciably reducing the evaporation of a fragrance B, and viceversa, or mixing the two fragrances, at user's will. The existing solutions to reduce evaporation of active substances through a membrane only consist in closing the housing around the cartridge (container of the volatile substance) but not the cartridge itself, so that evaporation induced by temperature can occur also, leading to:

- exit of the housing if the closure is not completely impermeable or
- condensation in the container if it is impermeable.

Existing devices do not provide effective means to appreciably reduce the evaporation of a substance. The present invention allows to appreciably reduce the evaporation of a substance whilst the evaporation of another substance is increased.

DESCRIPTION OF THE INVENTION

One embodiment refers to a volatile substance diffuser based on permeable membrane wherein a closing solid wall is applied to or separated from the membrane to stop or allow evaporation, respectively.

In one embodiment the position of the wall in the close position is below the welding flange of the membrane, in order to compensate possible vacuum inside the container.

One embodiment refers to a device with 2 containers and 2 respective closure systems which allows selecting the evaporation of fragrance A, fragrance B, or a mix of the two fragrances. Preferably the device is a car air-freshener.

One embodiment refers to devices for evaporating volatile substances in a closed environment, without the use of electric power, heating elements or absorption wicks, for the purpose of simplifying and maximally reducing the cost of the device, but at the same time maintaining its efficacy and also allowing the user to be able to select at will the fragrance to evaporate. For that purpose, the evaporator device uses a vapor permeable membrane as the element responsible for causing the evaporation of the product to be evaporated. The device can be used with the cooperation of an air current with a suitable temperature enhancing the evaporation and diffusion of the volatile substance, such as the ventilation air outlet of a vehicle, for example. The volatile substance consists in an air-freshening product, insecticide or the like.

In some embodiments, the evaporator device can use a vapour permeable membrane closing the volatile substance container. In a typical embodiment, the device can be used with the cooperation of an air flow with a suitable temperature enhancing the evaporation and diffusion of the volatile substance, such as the ventilation air outlet of a vehicle, for example.

In another embodiment, a fan or a heater can be combined with the membrane to enhance evaporation and diffusion of the volatile substance.

In some embodiments, the membrane can be sealed on the container on a single plane. Thus, by applying a flat closing wall against this particular flat perimeter of the membrane, impermeable closure can be achieved. The closing wall can be displaceable towards the membrane, that is reducing progressively the distance between the membrane and the closing wall.

One embodiment refers to a design of said closing wall to compensate the deformation of the membrane. In one embodiment, the closing wall gets, in the area that corresponds to the interior of the welding perimeter below the plane of the welding (inside the container).

In fact, permeable membrane cannot be considered as a perfectly flat plastic sheet as shown in FIG. 2(a), because several factors can lead to mechanical deformation of the membrane:

- relaxation of the plastic structure due to partial solubilisation of the plastic by the chemical product contained inside, see FIG. 2(b).
- inwards deformation due to the appearance vacuum inside the container (if the volatile substance that goes out through the membrane is not substituted by air) FIG. 2(c). Note in FIG. 3a right drawing the space (38) between the membrane and the closing wall wherein the evaporated product can accumulate.
- outwards deformation due to the weight of the chemical substance inside the container that exceed mechanical resistance of the film FIG. 2(d).

As commented above, the problem to have some space between the membrane and the closure is that evaporation can occur in such space, that may lead to condensation of vapour and accumulation of liquid if conditions of temperature and or pressure vary. This liquid may fall when closure wall is open subsequently.

The fact the closing wall gets inside the container, that means, below the plane of theoretical position of the membrane, permits to force the membrane to adapt to the shape of the closing wall and thus to avoid the formation of any free space in the closed device as described before regarding FIG. 2.

Some embodiments refer to a device for air freshening through a membrane wherein the closure of the membrane can be carried out by applying a closing wall. Preferably, the shape of the wall can be adapted to compensate possible deformation of the membrane.

Some embodiments refer to a method for adjustably evaporating two or more volatile substances, wherein it comprises putting said volatile substance in contact with two or more strips of vapour permeable material, projecting an air flow on said strips, controlling the air flow acting on said strips.

In a typical embodiment, the control of the air flow acting on each of said strips can be carried out by inserting or removing obstacles that the air flow must overcome prior to acting on said areas.

Some embodiments provide the following innovative aspects:
possibility of selecting the substances to evaporate through innovative presence of a selector and innovative shape of the selector (convex surface of the selector to match concave shape of the permeable strip).
possibility of mixing two fragrances/substances at user's will, thus allowing fragrance personalization. The device could be mechanically set at 3 stable points on the selector lever stroke so that only fragrance A, or fragrance B, or predefined mixing of fragrances A+B can be evaporated.
new way of controlling the degree of evaporation.
refillable or disposable.

DESCRIPTION OF THE DRAWINGS

To complement the description being made and for the purpose of helping to better understand the features of the invention, according to a typical embodiment thereof, a set of drawings is attached as an integral part of said description which, with an illustrative and non-limiting character, show the following:

FIG. 2 shows several side views of a container sealed with a membrane, wherein the membrane is deformed due to different factors.

FIG. 6 shows a sequence of several schematic figures wherein the closing wall is applied against the membrane in a progressive manner as indicated by the arrows.

DETAILED DESCRIPTION OF THE INVENTION

Figure 1B:
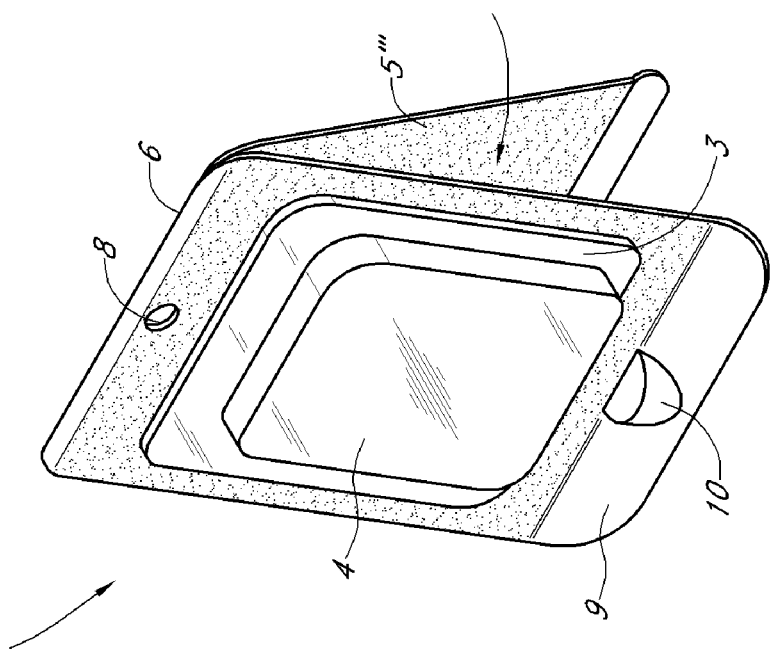
FIG. 1 shows air freshener devices and components.
Figure 1A:
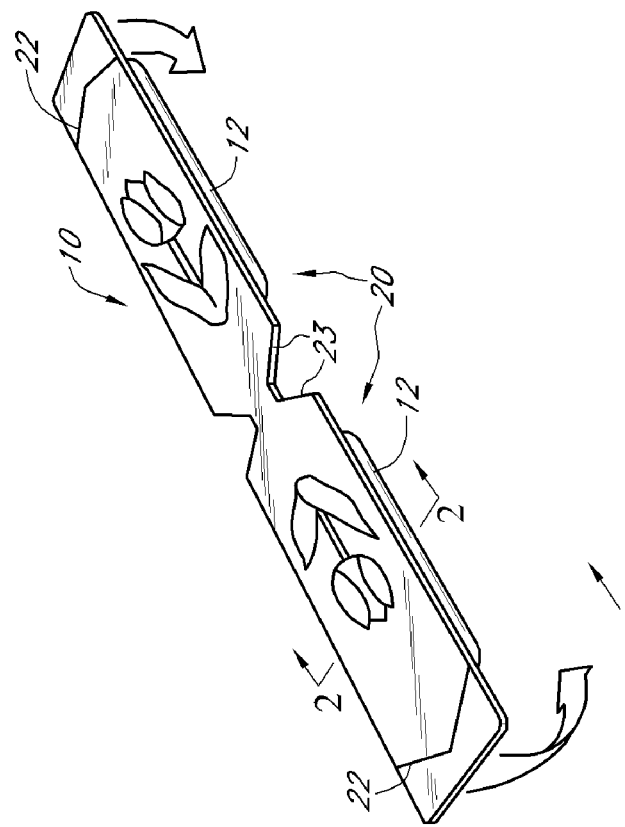
Figure 1C:
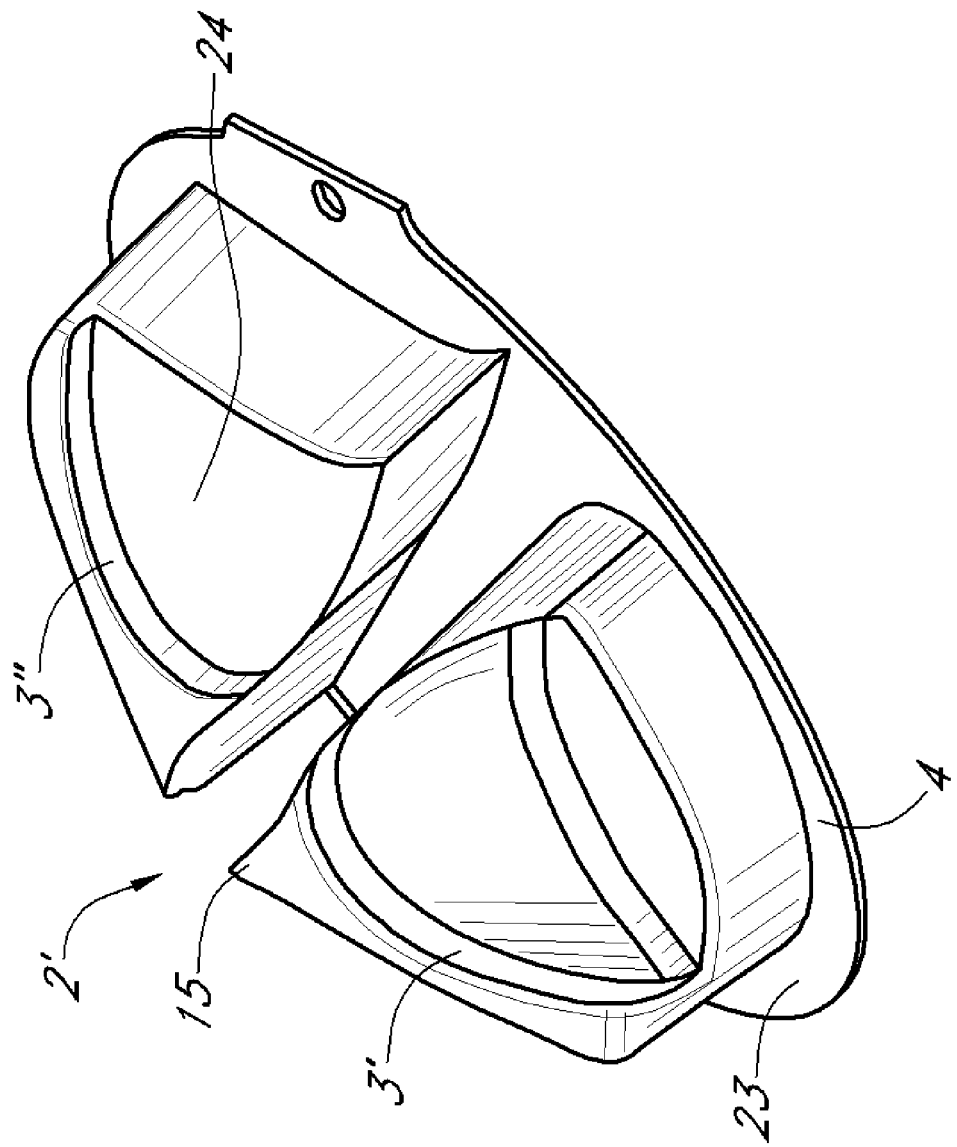
Figure 3A:
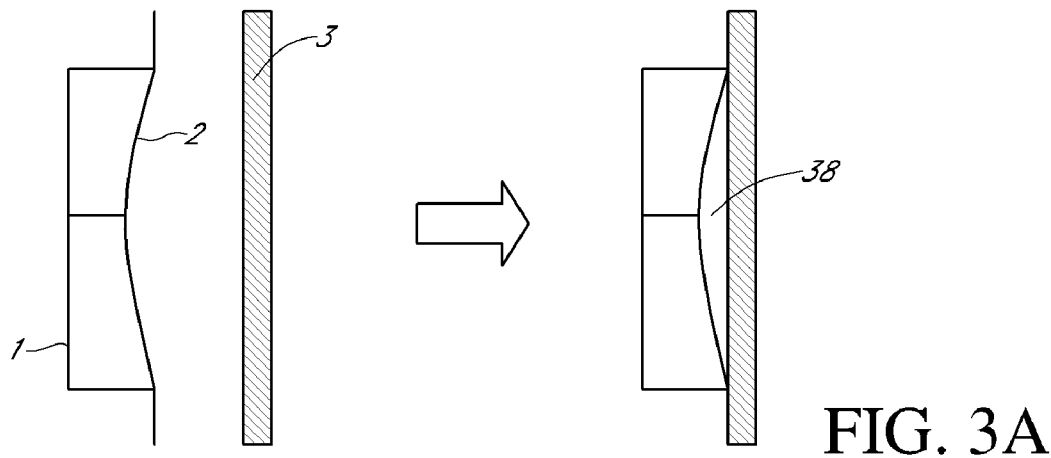
FIG. 3 shows several schematic side views of several designs of the closing wall. Figures at the right column shows the closing wall applied against the membrane.
Figure 3B:
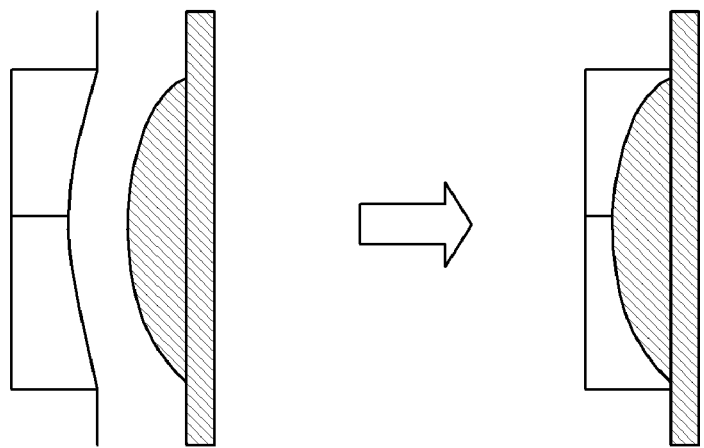
Figure 3C:
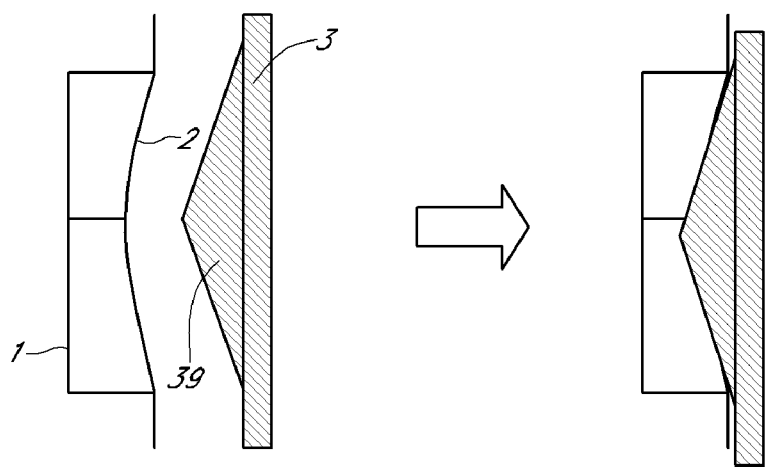

FIG. 3 shows several designs of the closing wall (3) according to one aspect the invention. It has the following features:
a peripherical rib that fit with the inner perimeter of the membrane (2) when the membrane is stressed against the closing wall (3).
a design with no negative area. (for example the closing wall has an inner face having one of the following shapes: triangular, Trapezoidal, semi spherical, semi elliptical, . . . ), as shown for instance in FIGS. 3b and 3c.
the geometry of the wall is designed in order to apply a strain lower than the elastic limit of the plastic material of the membrane (in dry condition).
the geometry of the wall is designed in order to apply a stress lower than the elastic limit of the plastic material of the membrane (conditioned with the chemical substance).

Figure 4:
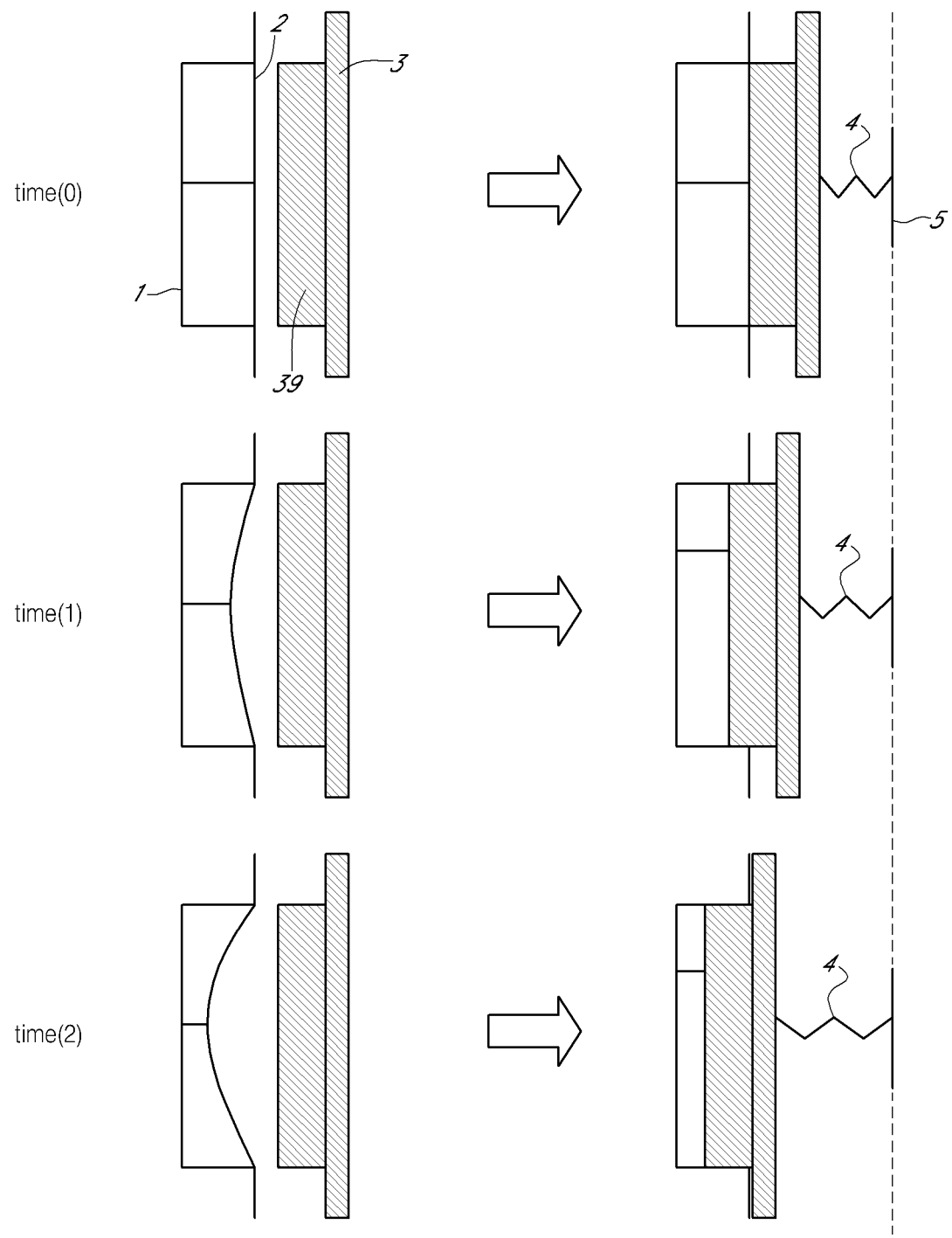
FIG. 4 shows several schematic side views of several designs of the closing wall biased by an elastic component. Figures at the right column shows the closing wall applied against the membrane.

In one embodiment, as shown in FIG. 4, is that the support of the closing wall has an elastic component (4) that permit the stress of the closing wall (3) not to exceed the elastic limit of the membrane.

This elastic component (4) can be a spring, having one end connected to a fixed element (5), and another end fixed to the outer face of the closing wall (3), so that the closing wall is pressed against the membrane by the spring.

The maximal stress applied by the spring should be lower than mechanical resistance of the membrane.

In FIG. 4 the spring is located in the side of the closing wall (3), but in other embodiments the spring could also be located at the opposite side that is the side of the container and also pulling the closing wall against the membrane.

Figure 5:
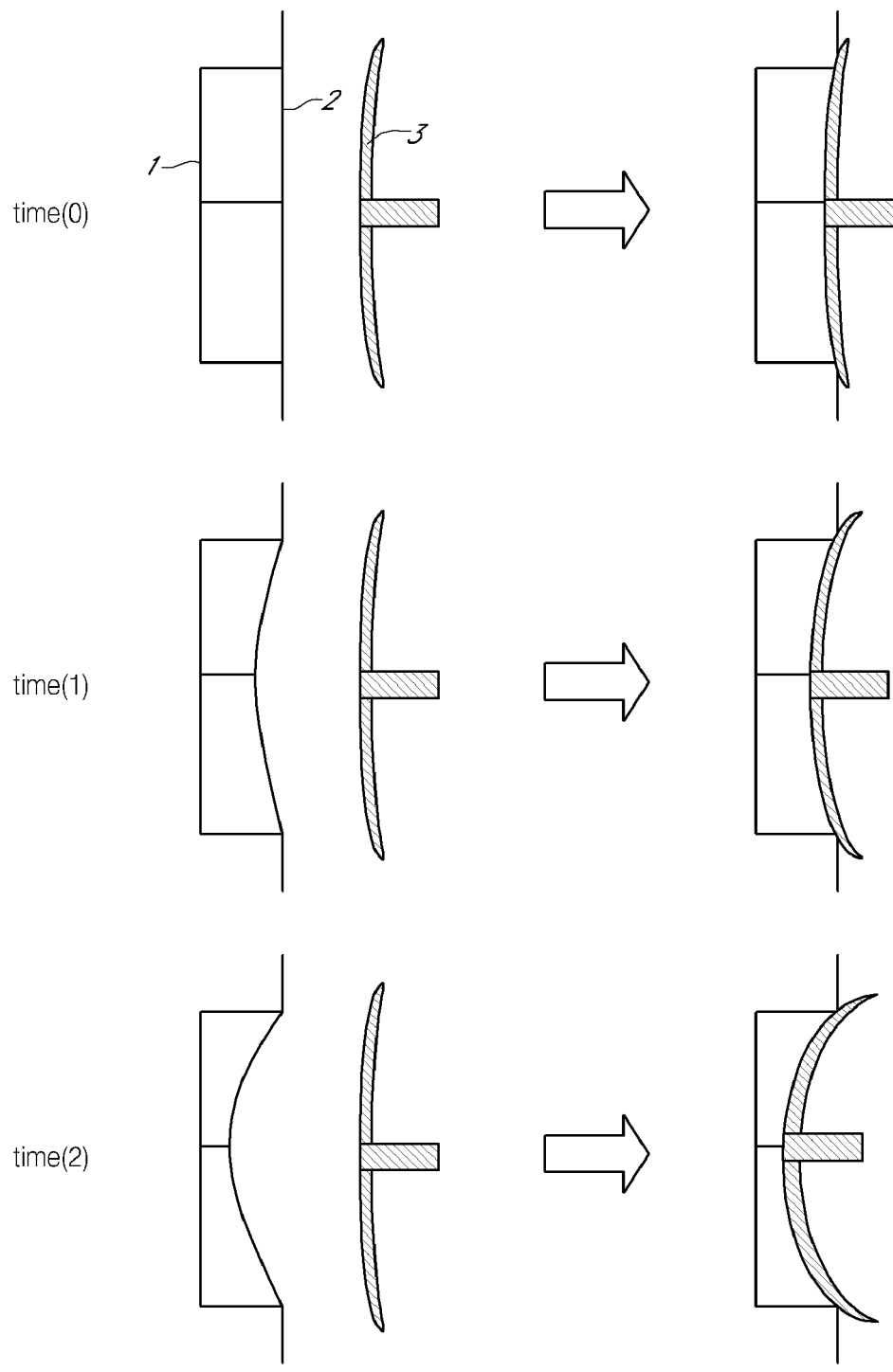
FIG. 5 shows several schematic side views wherein the closing wall is able to deform in order to adopt its shape to the membrane. Figures at the right column shows the closing wall applied against the membrane.

In one embodiment, as shown in FIG. 5, the closing wall (3) is able to deform in order to adopt its shape to the membrane.

Also, the application of the wall can be performed in a progressive way as shown in FIG. 6, in order to reduce but not stop the evaporation process. This way, a regulation of the performance of the device can be obtained. In FIG. 6 it can be observed that in the displacement of the closing wall, there is established a closed position (FIG. 6d) in which the membrane is completely covered by the closing wall, an open position (FIG. 6a) in which the membrane is in contact with the air, and an intermediate position (FIGS. 6b, 6c) in which the membrane is partially covered by the closing wall. Regulation of the degree of evaporation of the volatile substance is thereby achieved.

Figure 7A:
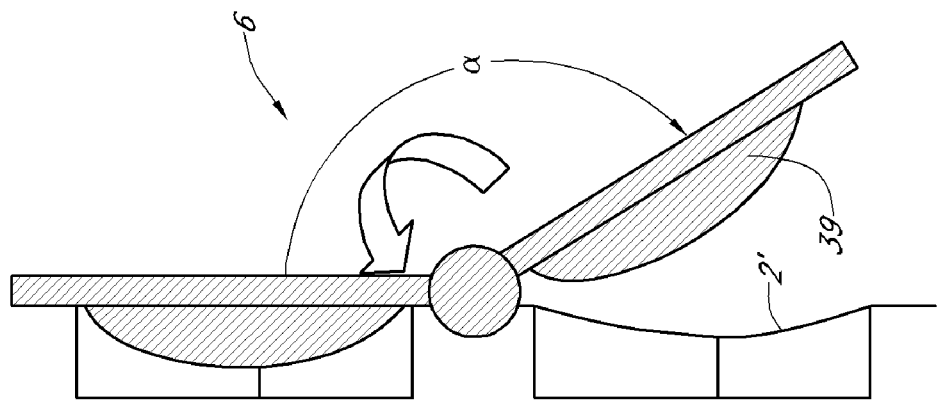
FIG. 7 shows two schematic side views of an air-freshening device having a double cartridge and double closing wall.
Figure 7B:
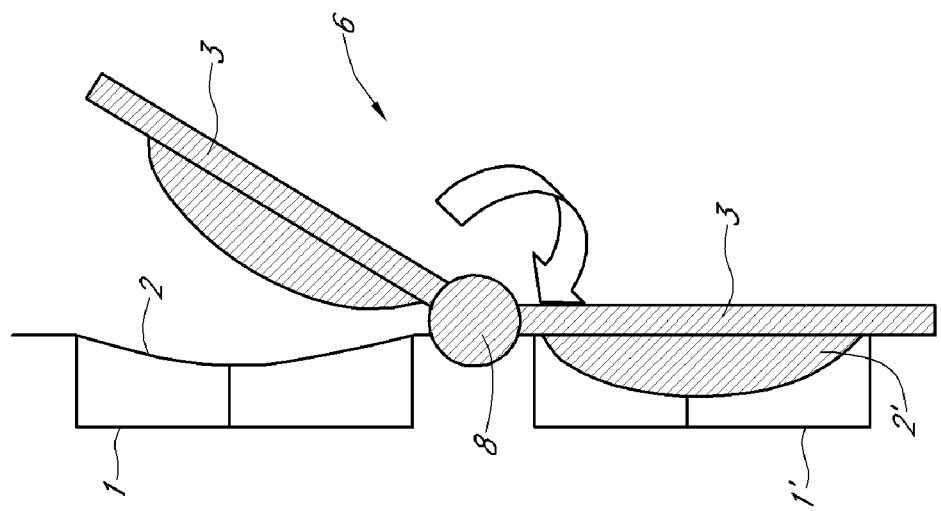

In one embodiment, as shown in FIG. 7, refers to an air-freshening device having a double cartridge.

The device has two or more strips of vapour permeable material (2,2'), in which an air flow with a suitable temperature cooperates in the evaporation of two or more volatile substances, which comprises two or more containers (1,1') for at least two types of volatile substances in contact with said vapour permeable material (2,2'), which is exposed to said air flow.

The device also comprises a casing (7) (see FIG. 8) supporting said containers (1,1') and said vapour permeable strips (2,2'), and keeps them under the influence of said air flow. The device also has means (6) for selecting the volatile substances to be evaporated by means of allowing or stopping the air flow acting on either vapour permeable strip (2,2'). Said means (6) for selecting the volatile substances, may consist of two closure walls (3,3') interconnected, in such a way that when one wall is closing the corresponding permeable strip, the other wall is spaced apart from its corresponding permeable strip leaving the strip accessible.

In particular the two closing walls (3,3') defining the means (6) for selecting the volatile substances, define an angle ($\alpha$) in between and are interconnected at a pivoting point (8). The closing walls (3,3') are pivotally mounted in respect to the pivoting point (8) for selectively closing one of the permeable membranes (2,2').

The shape of each closing wall (3,3') is also adapted to compensate possible deformation of the associated membrane (2,2'). In this case, this is achieved by a curved abutment or protuberance (39) provided in the inner face of the closing walls.

Said air flow can be typically at a temperature suitable for enhancing the evaporation of said substances. Suitable temperature must be understood as any temperature having the effect of speeding up the degree of evaporation of the substances.

The vapour permeable strips are liquid impermeable evaporation membranes adhered to said containers (1,1') for the volatile substances forming an air-freshening unit, such that one of the faces of each strip is partially in direct contact with the respective volatile substance, and the other face is partially in direct contact with the environment. Volatile substances are preferably aromatic substances, although substances with another type of properties, such as insecticide substances for example, can also be used.

The fragrance selection means (6) are placed between the air flow and the external face of the permeable strip.

In some embodiments, the device can be complemented with means for fixing to a fixed structure (for example a hook (9) in FIG. 8), such as the grating of a ventilation air equipment outlet, for example, such as the ventilation air outlet of a motorized vehicle (10), or an air conditioning equipment.

In such case, the aforementioned air flow comes from the ventilation air outlet of a vehicle, or of an air conditioning equipment.

The hook (9) allows to place the device in 0° to 360° position, with clicks in correspondence of some position (e.g. 0°, 45°, 90°, 135°, 180°).

As it can be observed in FIG. 8, one embodiment provides an evaporator device of great simplicity, and therefore of a very reduced cost, is thus obtained, such that it can be used and disposed of, i.e. single use. Alternatively, the parts forming said casing (7) can be opened for the purpose of replacing the air-freshening unit (11) when the volatile has been consumed.

In view of FIG. 8, it can be seen how in a typical embodiment, the evaporator device comprises an air-freshening unit (11) formed by two independent containers (1,1') housing the volatile substances to be evaporated, which are preferably in a liquid state. The containers (1,1') are hermetically sealed by an evaporation membrane (2,2') such that each volatile substance is in direct contact with one majority part of the internal face of the respective membrane (2,2'), which is liquid impermeable such that it prevents any spillage, but is vapor permeable, therefore allowing the evaporation of the liquid it retains. The containers (1,1') are manufactured from a heat-formed plastic material.

A protective strip (25) is arranged on the outer face of the membranes (2,2'), preventing the evaporation of the substance prior to using the device, for which purpose said strip is easily removable and partially extends outside of the device, forming a tab facilitating its removal after removing the front part for being able to access it. This protective strip (25) must be partially folded over itself and project on one side, such that the protective strip (25) can be easily removed from that side from the exterior of the product without needing to open the housing (7).

In one embodiment, as shown in FIG. 8, the device comprises a housing (7) and a fragrance selector (26) formed by the double closing wall (3,3').

The selector projects outside with a lever (similar to the knob 34 in FIG. 13) that allows to set the evaporation of substance A, or to set the evaporation of substance B, or to set an adjustable mixing of the two substances. In order to allow such control the inner part of the selector is placed between the air flow and the outer face of the permeable strips.

The housing (7) is closed by snapping or differently coupling its upper part to its lower part or by other conventional means and the air-freshening unit (11) is enclosed inside the assembly, as seen in the figures. Said coupling can be stable, in which case the device will be a single-use device, i.e. to use and dispose of. Optionally, the coupling can be removable so as to allow replacing the air-freshening unit with a spare part when the air-freshening liquid is used up. The front part of the housing (7) is provided with a holes (27,28) through which the containers (1,1') of the air-freshener unit (11) are visible.

To enhance the appearance of the device the containers can be transparent and the volatile substances housed therein can be coloured, for example with a colour associated to the aroma each of said substances releases.

Since the device is especially indicated for use thereof under the influence of a hot air current, the materials with which it is manufactured, and particularly the materials of the containers (1,1'), have been carefully selected to withstand temperatures comprised between 75 and 80° C.

The surface of the selector (26) in contact with the permeable strip, or expected to be in contact with the permeable strip following user's actuation on the selector (26), is convex such that the surface of the selector can almost match the concave permeable strip in front of the respective container that lost its original planar shape during the use, due to pressure decrease inside the container following the evaporation of the liquid contained therein.

Figure 8A:
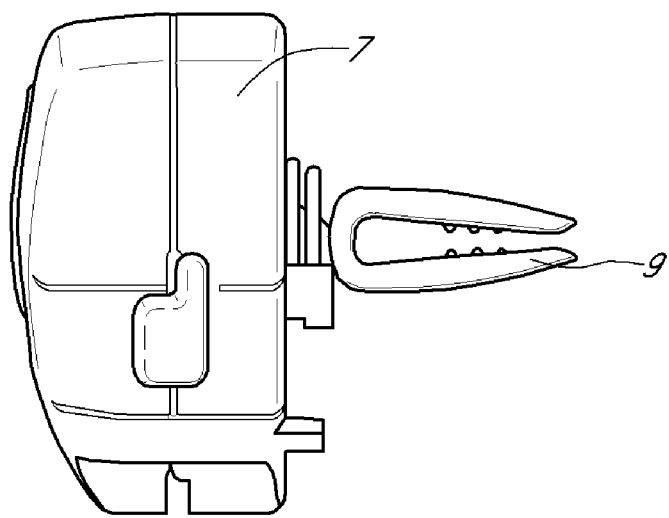
FIG. 8 shows several images of a typical embodiments, wherein figure (a) is a side view, figure (b) is a front view, figure (c) consist of two cross-sectional views taken from line (A-A) in figure (b) with different positions of the selector, figure (d) is a top view, figure (e) is a perspective view of the air-freshening unit (note the refill peeling tab coming out from the left side), and figure (f) is a perspective view of the device fixed to a ventilation grating of a vehicle (vertical:left, horizontal,right figure).
Figure 8B:
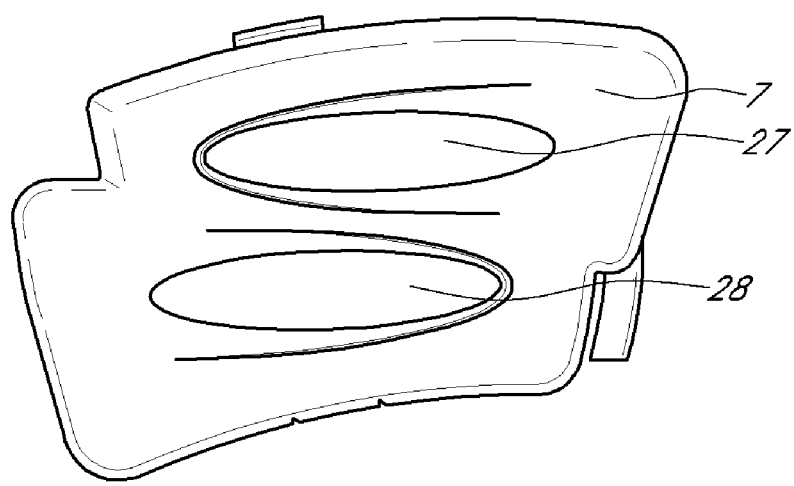
Figure 8C:
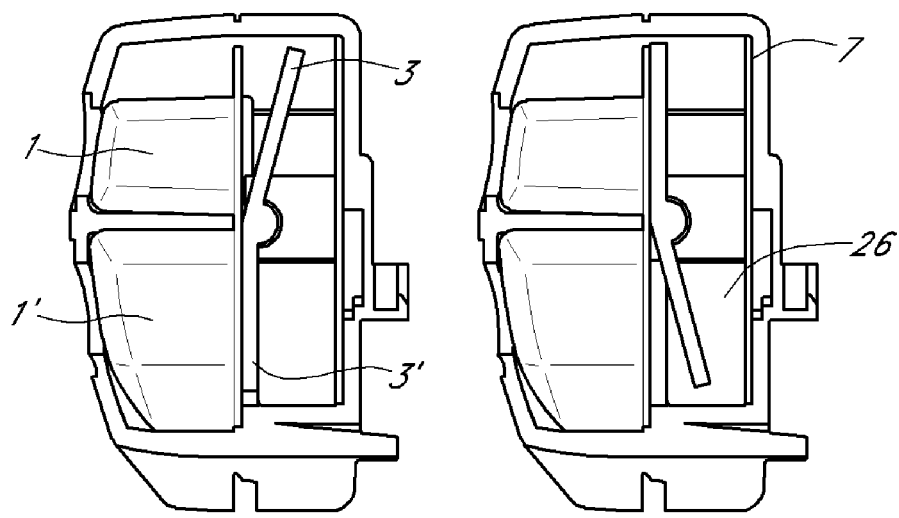
Figure 8D:
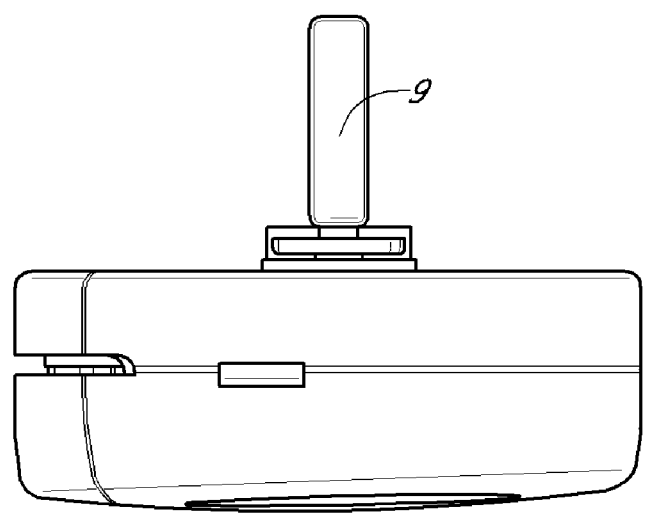
Figure 8E:
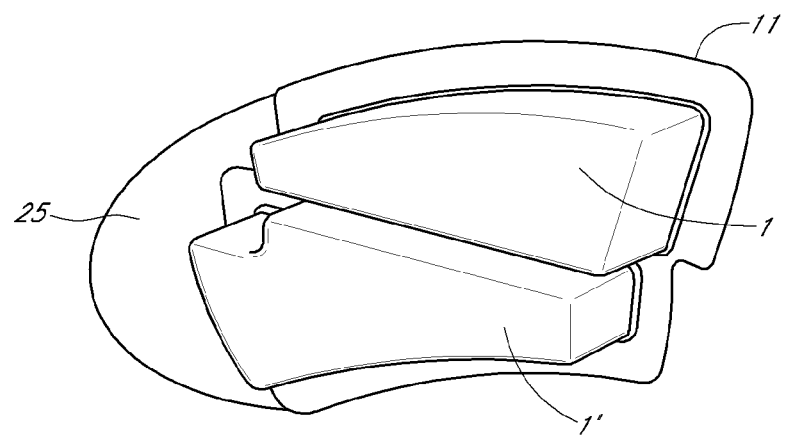
Figure 8F:
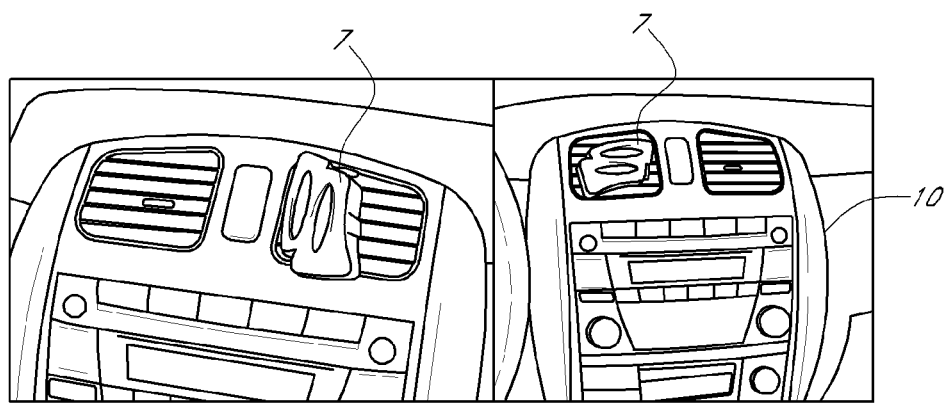

The device comprises fixing means (9) for fixing it to a fixed structure, such as the grating (10) of the air outlet of a ventilation unit of a vehicle, as shown in FIG. 8*f*, such that the device is emerged in the air current generated, part of which passes through the device. In a similar manner, the device could be applied on an air-conditioning equipment.

The device is complemented with fixing means for fixing it on said grating, consisting in flexible tabs which, acting like a gripping device, can be stably coupled to said grating. The resilient tabs are integral to the intermediate part and pass through the rear part (8) through a hole, such that this intermediate part remains fixed during the adjustment and the rear part is the part which rotates to cause the adjustment.

The evaporated product is diffused towards the sides of the device in 360°, for which purpose it has at least one side slot, and rear windows which allow the air current to enter or circulate impelling the evaporated product.

A graduated scale allows the user to identify the degree of opening of the windows and therefore the degree of evaporation selected between a maximum and minimum for each fragrance.

The device can be placed on a horizontal as well as vertical grating.

In this typical embodiment, it is seen how in the device, the membrane adopts a transverse arrangement with regard to the feed direction of the air flow. However, in other possible embodiments, said arrangement of the membrane could have a certain tilt with regard to the air flow.

Figure 9A:
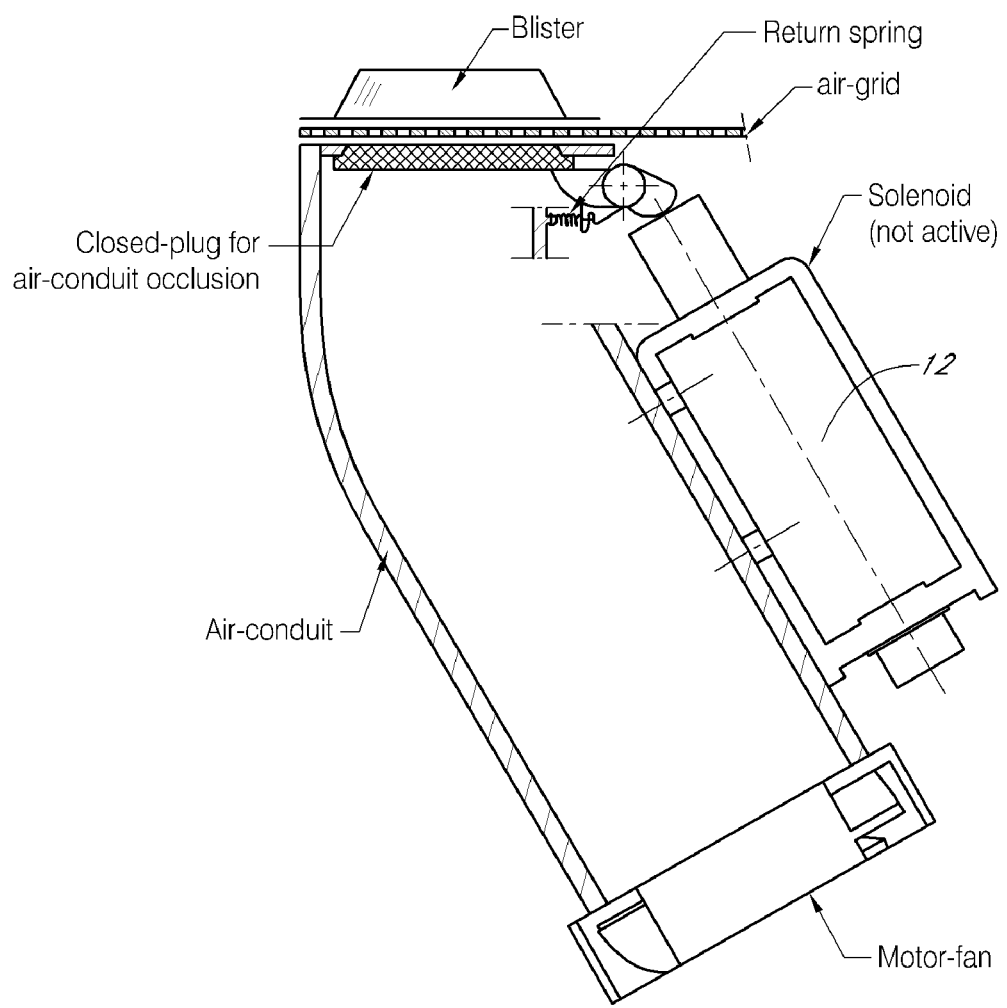
FIG. 9 shows two cross-sectional side views of a device according to a typical embodiment of the invention, wherein figure (a) shows the device in a stand-by position (closed), and figure (b) shows the device in operation (open).
Figure 9B:
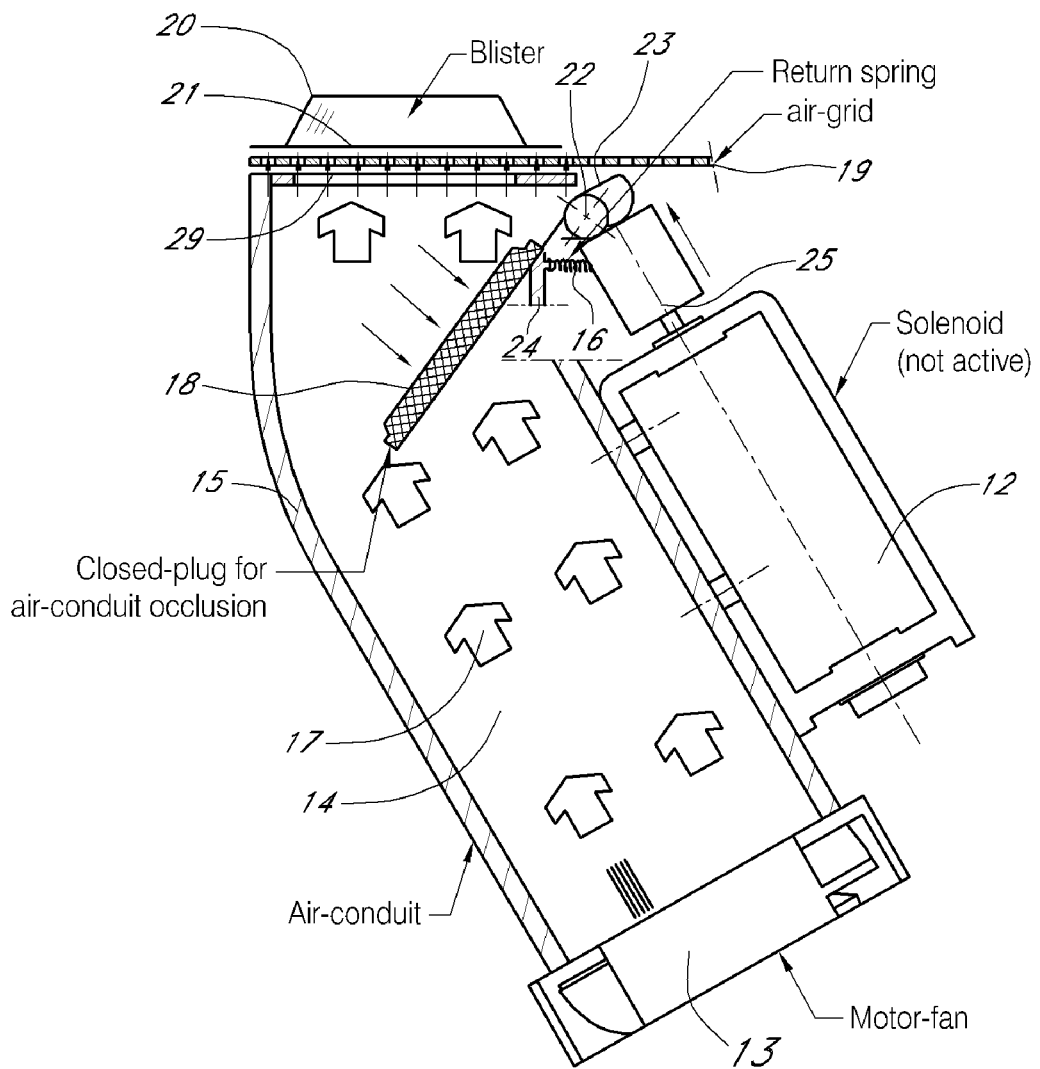
Figure 10:
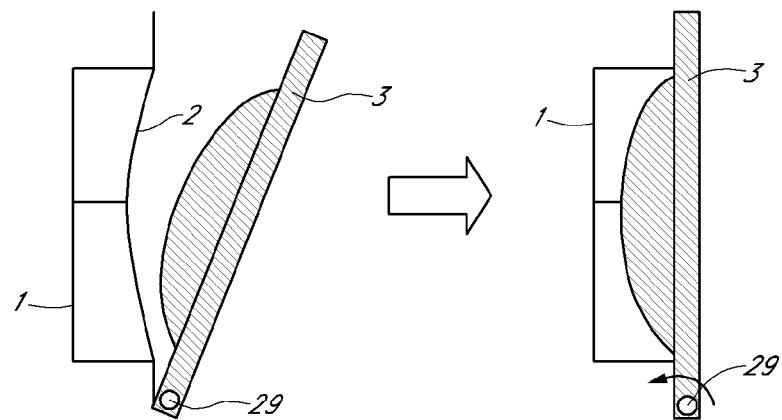
FIG. 10 shows two side views of a container with membrane and a closing wall pivotally mounted about a shaft (29) for opening and closing the membrane while pressing the membrane at the same time. The closing wall can be moved manually or by any actuation mechanism.

In one embodiment, as shown in FIG. 9, the evaporation surface of the membrane is also closed by applying a rigid flat wall against the membrane surface, however the movement of the wall is performed by an electromagnetic actuator (12).

The device of FIG. 9 comprises a casing (15) defining internally an air passage (14) wherein a fan (13) generates a forced current or air (17). The fan (13) is arranged at one end of the air passage (14), whereas at the other end of the passage (14) there is an opening (29) and an air-grid (19) located on said opening (29). A container (20) of a volatile substance with a membrane (21), is arranged at said opening so that the membrane receives the forced current or air (17). A closing wall (18) is provided for closing and opening said opening (29) so that to allow the membrane to receive the flow of air for the evaporation of the substance, or to close the membrane and avoid said evaporation.

Said closing wall (18) is operated by a displacement element, in this case a solenoid or electromagnetic actuator (12) for closing and opening said opening (29).

A cam element (23) is pivotally mounted on a shaft (22), and the closing wall (18) is joined to one part of the cam. The actuation element (25) of the electromagnetic actuator (12) is displaced to move the cam thus producing a pivoting movement of the closing wall about said shaft. The cam element (23) is biased by a return spring (16) connected to a fixed point (24).

Figure 11:
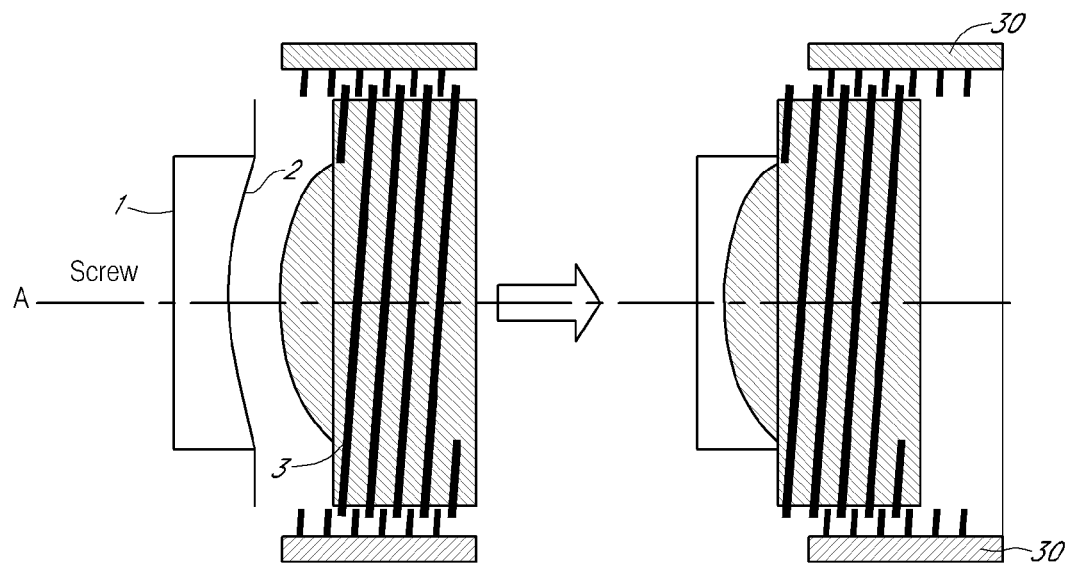
FIG. 11 shows two side views of a container with membrane and a closing wall operated by a screw mechanism.

In the case of FIG. 11, the closing wall (3) is arranged to move longitudinally along a longitudinal axis (A) of the membrane (2). The closing wall is displaced by means of a screw mechanism to move forward and backwards in respect to the membrane (2). The closing wall can be moved manually or by a suitable actuation mechanism. The closing wall (3) is housed within a cylinder (30) and it is screwed with the internal wall of said cylinder.

Figure 12:
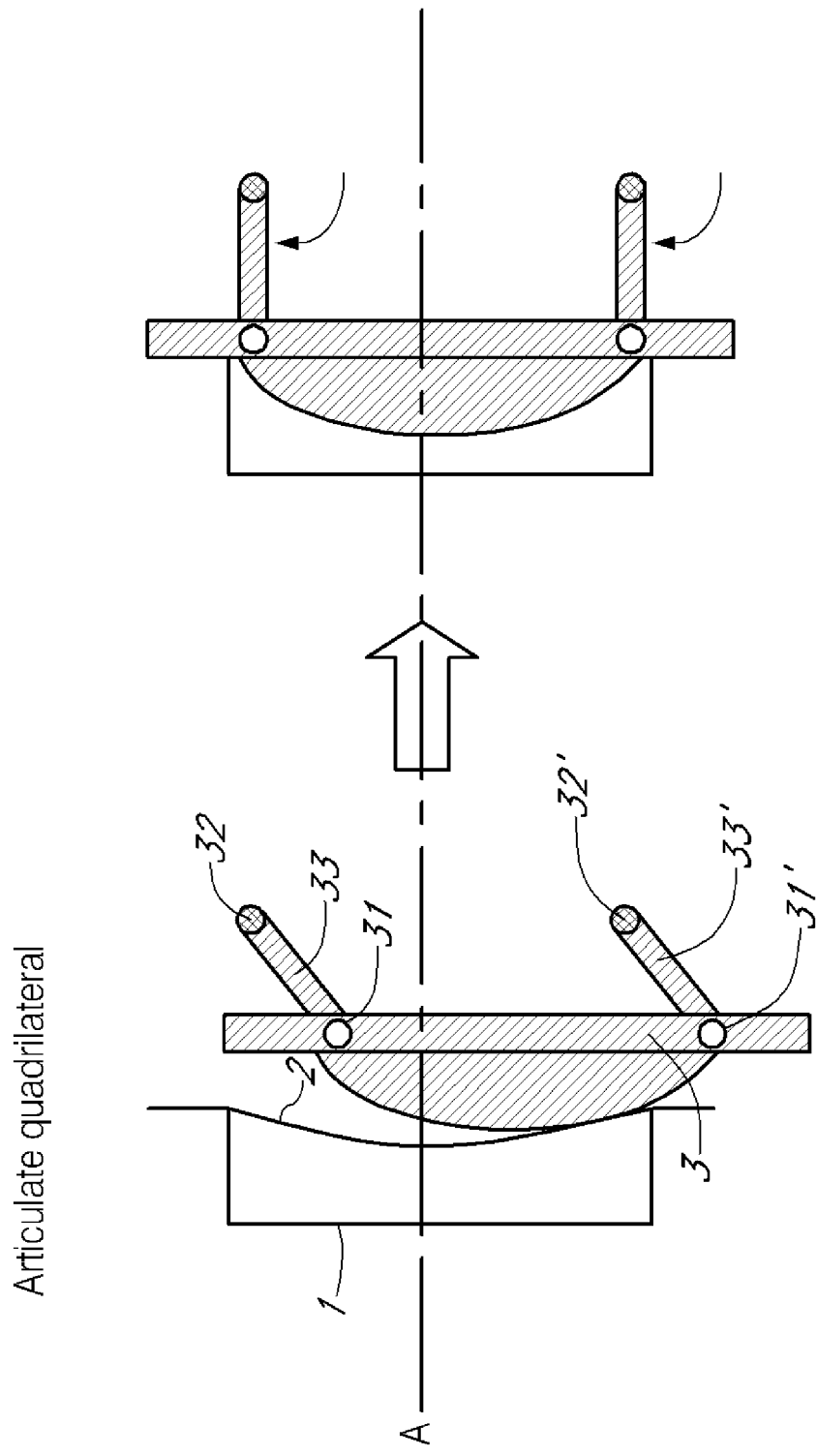
FIG. 12 shows two side views of a container with membrane and a closing wall operated by a articulated quadrilateral mechanism.

In one embodiment, as shown in FIG. 12, the closing wall is arranged to move transversally in respect to the axis (A) of the membrane by means of an articulate quadrilateral. The closing wall is joined to the ends of first and a second arms (33,33') at a fist and second articulated points (31,31') at said closing wall. A second end (32,32') of said arms (33,33') are articulately joined to a fixed point. Therefore the closing wall is pivotally mounted in respect to the two articulation points (32,32').

Figure 13:
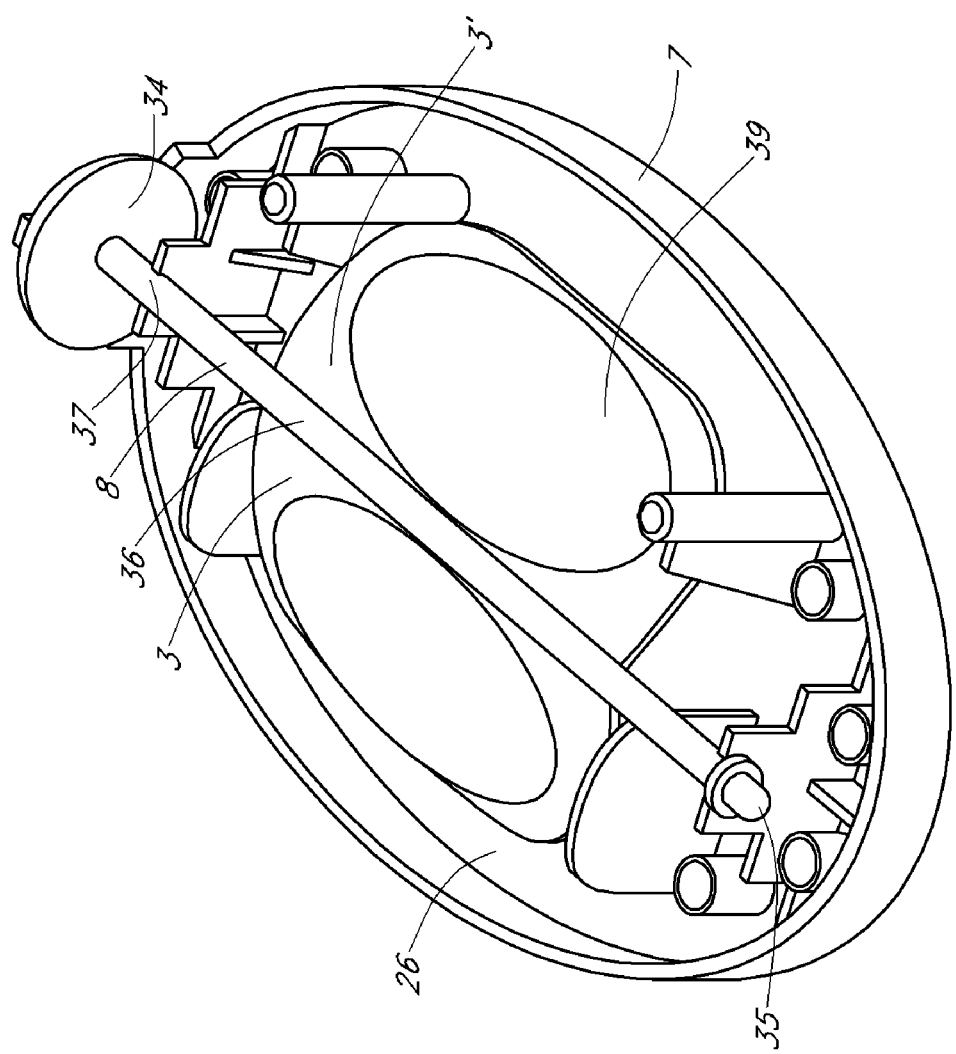
FIG. 13 shows a perspective view of a typical embodiment of the invention without containers and in which a part of the casing of the device removed for illustration purposes.
Figure 14:
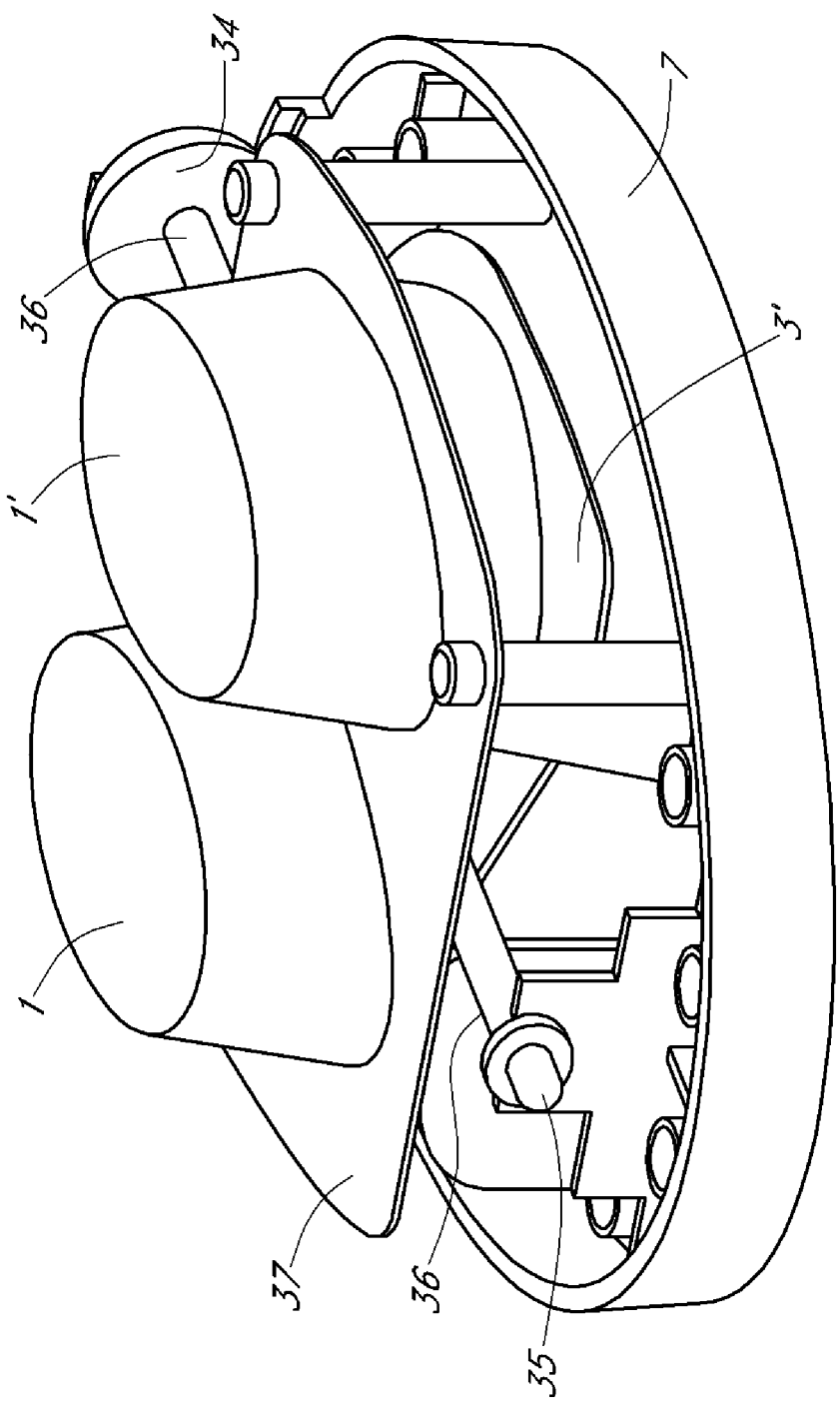
FIG. 14 shows another perspective view of the device of FIG. 13.
Figure 15:
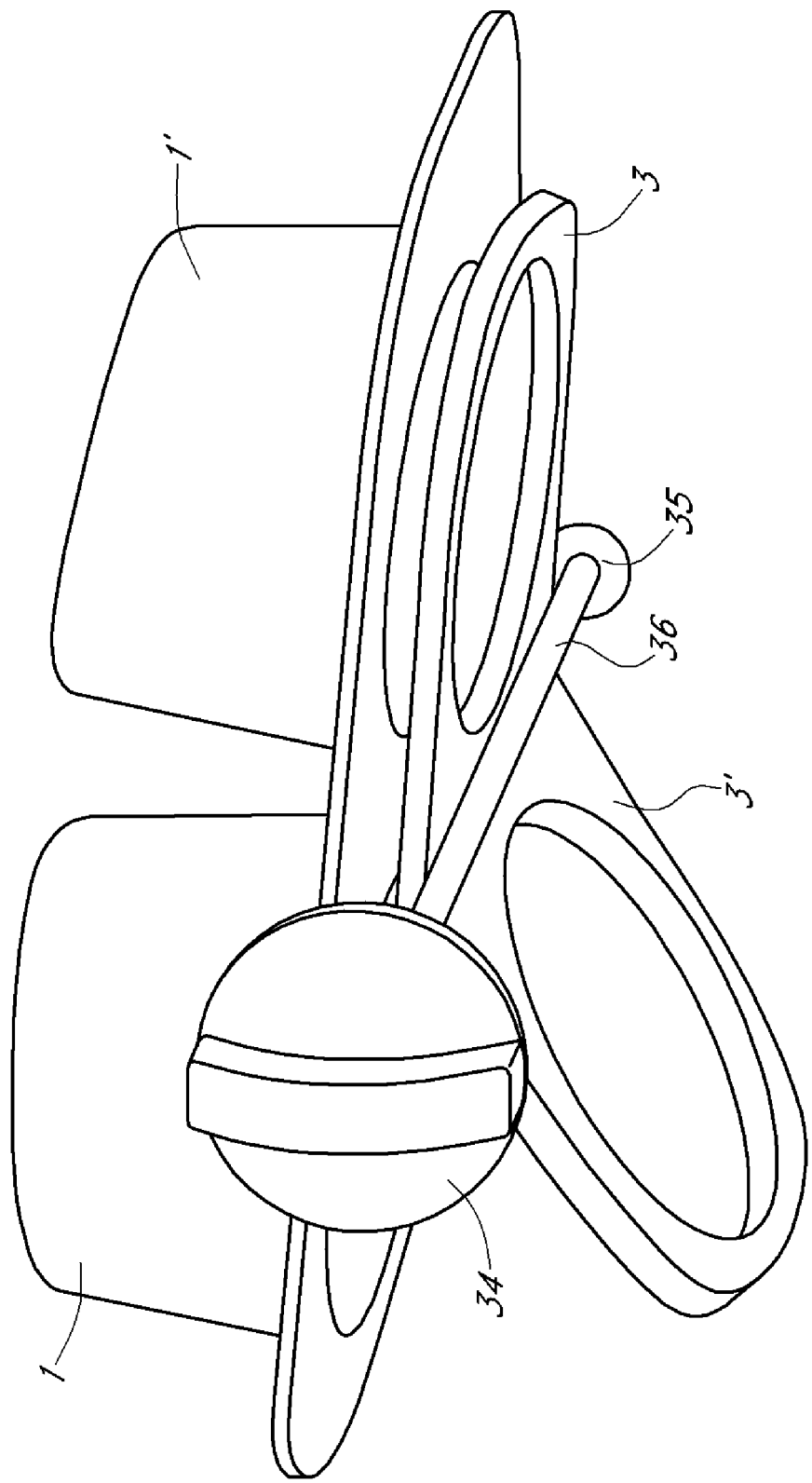
FIG. 15 shows another perspective view of the device of FIG. 13 without the casing.

In one embodiment, as shown in FIGS. 13, 14 and 15, a fragrance selector element similar to the one shown in FIG. 8 has been incorporated. The device of FIGS. 13-15 comprises a double container having a first and second containers (1,1') protruding from a common and flat plastic plate (37) which is fixed to the casing (7) of the device.

The fragrance selection element (26) consist of a first closing wall (3) and a second closing wall (3') both joined to a pivoting point (8) defined by a straight rod (36). The walls (3,3') define an angle in between and in respect to said rod (36).

The rod (36) is rotatably mounted on the casing (7) at its first and second ends (35,37), in such a manner that the first and second walls (3,3') are arranged to alternatively close one of the containers (1,1') as it can be more clearly observed on FIG. 15. A knob (34) is joined to one end of the rod (36) and protrudes outside of the casing (7), so that the user can manually rotate the rod (36) to close one the containers (1,1') by locating the corresponding closing wall in the entry of the container, thereby selecting the desired fragrance or product to be evaporated.

Some embodiments refer to a method for adjustably evaporating two volatile substances, which comprises putting said volatile substances into contact with two strips of vapor permeable material, respectively, and projecting an air flow on said strips, controlling the air flow acting on each strip and, as a result, the amount of each evaporated substance projected into the environment.

Control of said air flow acting on said strip is carried out by modifying the area which the air flow must pass through before acting on each strip.

Modification of the area for the passage of the air flow can be carried out by moving two parts, relatively to one another, making one part to cover each said strip by a greater or lesser extent thus decreasing or increasing the area available for the air flow.

The degree of evaporation of the substance is also adjusted by means of controlling, either in a natural or forced manner, the temperature of the air flow.

In view of this description and set of figures, a person skilled in the art could understand that the embodiments of the invention which have been described can be combined in multiple manners within the object of the invention. The invention has been described according to several preferred embodiments thereof, but for the person skilled in the art it will be evident that variations can be introduced in said preferred embodiments without exceeding the object of the claimed invention.

What is claimed is:

1. Volatile substance diffusing device comprising at least one container of a volatile substance and a semi-permeable membrane, closing said container which allows passage of the volatile substance in a gaseous state, wherein the device further comprises at least one movable closing wall arranged for closing and opening said membrane, wherein the shape of said at least one closing wall is adapted to compensate possible deformation of the membrane.

2. The device according to claim 1 wherein the closing wall has an abutment in its inner face, and wherein the closing wall is displaceable to a where said abutment presses the membrane to the interior of the container.

3. The device according to claim 1 wherein the closing wall is made of a flexible material.

4. The device according to claim 1 wherein the closing wall is longitudinally displaceable against the membrane.

5. The device according to claim 1 wherein the closing wall is biased against the membrane by means of an elastic element.

6. The device according to claim 1 wherein the displacement of the closing wall, there is established a closed position in which the membrane is completely covered by the closing wall, an open position in which the membrane is in contact with the air, and an intermediate position in which the membrane is partially covered by the closing wall.

7. The device according to claim 1 wherein the closing wall is pivotally mounted in the device.

8. The device according to claim 1 wherein it further comprises a screw mechanism engaged with the closing wall for moving it.

9. The device according to claim 1 wherein the closing wall is transversally displaceable in respect to the longitudinal axis of the membrane.

10. The device according to claim 1 wherein it comprises an electromagnetic actuator for moving the closing wall.

11. The device according to claim 1 wherein it comprises a fan arranged for generating an air flow towards the membrane.

12. The device according to claim 6 wherein the closing wall has an abutment in its inner face, and wherein in the closed position the abutment of the closing wall is at least partially inside the container.

13. The device according to claim 1, further comprising a fixing means for fixing it to a fixed structure.

14. The device according to claim 1, further comprising a casing with rear and/or side slots facilitating the air inlet and outlet.

15. Volatile substance diffusing device comprising two containers of volatile substances and two semi-permeable membranes respectively joined to said containers, said semi-permeable membranes allowing passage of the volatile substance in a gaseous state, the device further comprising two movable closing walls configured so as to selectively close one of said membranes;
wherein the shape of said two closing walls is adapted to compensate possible deformation of the membrane.

16. The device according to claim 15 wherein said device comprises two joined closing walls, the closing walls defining an angle in between, the closing walls configured so as to selectively close one of said membranes.

17. The device according to claim 15 wherein the closing walls have an abutment in an inner face of said device, and wherein the closing walls are displaceable to where said abutment presses the membrane to the interior of the container.

18. The device according to claim 15 wherein the closing walls are made of a flexible material.

19. The device according to claim 15 wherein the displacement of the closing walls, there is established a closed position in which the membrane is completely covered by the closing wall, an open position in which the membrane is in contact with the air, and an intermediate position in which the membrane is partially covered by the closing wall.

20. The device according to claim 15 wherein the closing walls are pivotally mounted in the device.

21. The device according to claim 15 wherein the closing walls is transversally displaceable in respect to the longitudinal axis of the membrane.

22. The device according to claim 15 wherein said device comprises an electromagnetic actuator for moving the closing walls.

23. The device according to claim 15 wherein said device comprises a fan arranged for generating an air flow towards the membranes.

24. The device according to claim 15 wherein in the closed position the abutment of the closing walls is at least partially inside the container.

25. The device according to claim 15 further comprising a fixing means for fixing said device to a fixed structure.

26. The device according to claim 15 further comprising a casing with rear and/or side slots facilitating the air inlet and outlet.

* * * * *